United States Patent
Kolb et al.

(10) Patent No.: US 6,806,380 B2
(45) Date of Patent: Oct. 19, 2004

(54) MODIFIED SAFE AND EFFICIENT PROCESS FOR THE ENVIRONMENTALLY FRIENDLY SYNTHESIS OF IMIDOESTERS

(75) Inventors: Hartmuth C. Kolb, East Windsor, NJ (US); Ramanaiah C. Kanamarlapudi, Bridgewater, NJ (US); Paul F. Richardson, Monmouth Junction, NJ (US); Gaznabi Khan, Caldwell, NJ (US)

(73) Assignee: Lexicon Pharmaceuticals, Inc., New Brunswick, NJ (US)

( * ) Notice: Subject to any disclaimer, the term of this patent is extended or adjusted under 35 U.S.C. 154(b) by 0 days.

(21) Appl. No.: 10/263,234

(22) Filed: Oct. 2, 2002

(65) Prior Publication Data

US 2003/0153728 A1 Aug. 14, 2003

Related U.S. Application Data

(60) Provisional application No. 60/326,662, filed on Oct. 2, 2001.

(51) Int. Cl.$^7$ .............................................. C07C 249/00
(52) U.S. Cl. ............................................................. 558/6
(58) Field of Search ............................................. 558/6

(56) References Cited

PUBLICATIONS

Database CAPLUS on STN, Acc. No. 1992:128187, EP 463676, Jan. 2, 1992 (abstract).*
Database CAPLUS on STN, Acc. No. 1979:611002, Pantev et al., Farmatsiya (Sofia, Bulgaria) (1979), 29(2), p. 1–5 (abstract).*
e–ROS, electronic Encyclopedia for Organic Synthesis, 2001–2003, John Wiley & Sons, Hydrogen Chloride, p. 1–15, http://www.mrw.interscience.wiley.com/eros.*

* cited by examiner

*Primary Examiner*—Brian Davis
(74) *Attorney, Agent, or Firm*—McDonnell Boehnen Hulbert & Berghoff LLP

(57) ABSTRACT

Disclosed is a safe, efficient and environmentally friendly method for preparing imidoesters.

17 Claims, No Drawings

MODIFIED SAFE AND EFFICIENT PROCESS FOR THE ENVIRONMENTALLY FRIENDLY SYNTHESIS OF IMIDOESTERS

This application claims benefit of Provisional 60/326,662 filed Oct. 2, 2001.

BACKGROUND OF THE INVENTION

1. Field of the Invention

This invention relates to a safe, efficient and scalable process for preparing imidoesters without the use of hydrogen chloride gas.

2. Description of the Related Art

Imidoesters, also known as imino esters, imidates and imino ethers, are useful building blocks for the synthesis of heterocyclic ring systems, such as oxazoles, imidazoles and their benzo-derivatives. They are also useful intermediates in the conversion of nitrites to esters and for the preparation of amidines, which are important heterocyclic building blocks. March, J. in "Advanced Organic Chemistry," 3$^{rd}$ edition, pp 792–793, John Wiley and Sons, New York, 1985.

Imidoesters are typically synthesized via the Pinner reaction, wherein a nitrile and an alcohol in an anhydrous solvent are treated with a large excess of anhydrous hydrogen chloride gas. See, for example, Roger, R.; *Chem. Rev.* 1961, 61, 179, *Organic Synthesis Coll. Vol.* 2, 284 (1943), and Dox, *Org. Synth. Coll. Vol.* 1, 5 (1941). However, a base catalyzed method for producing imidoesters has been disclosed. Schaefer, F. C.; Peters, G. A. *J. Org. Chem.*, 1961, 26, 412.

A significant defect with this method is the use of a large excess of the highly toxic, corrosive, and hard to handle hydrogen chloride gas. In the laboratory setting, it can be very difficult to determine exactly how much gas has been added to the reaction mixture, and consequently, a large excess of this very corrosive reagent is invariably used.

A method is desired for the preparation of imidoesters that uses the safer hydrogen chloride solutions, which are easy to handle, made by highly trained individuals using very safe, industrial procedures, and contain a well defined amount of hydrogen chloride per unit volume of solvent. Pre-made hydrogen chloride solutions are also economical because large excesses of the solutions are not required.

SUMMARY OF THE INVENTION

This invention provides for a safe and economical process for preparing imidoesters from nitrites. Specifically, the method of the present invention calls for the treatment of an anhydrous mixture of nitrile, alcohol, and solvent with anhydrous hydrogen chloride solution to form an imidoester. These compounds are useful building blocks for the synthesis of heterocyclic ring systems, such as oxazoles, imidazoles and their benzo-derivatives. They are also useful intermediates in the conversion of nitrites to esters. Specifically, the method comprises:

A) treating a nitrile with an anhydrous hydrogen chloride solution and an anhydrous alcohol, and
B) isolating the imidoester salt.

DETAILED DESCRIPTION OF THE INVENTION

According to Scheme 1, a preferred embodiment of the present invention relates to a method for the formation of an imidoester (iii) by treating an anhydrous mixture of a nitrile (i) and an alcohol (ii) with hydrogen chloride solution. The desired product is then obtained by reducing the volume of the reaction mixture, triturating with an ether, and filtering.

Scheme 1

According to Scheme 1:

R is $C_1$–$C_{10}$ alkyl or $C_3$–$C_8$ cycloalkyl, each of which is unsubstituted or substituted with one, two, three, four, or five groups independently selected from the group consisting of lower alkyl, lower alkoxy, aryl, arylalkyl, trifluoromethyl, trifluoromethoxy, $C_3$–$C_8$ cycloalkyl, and $C_3$–$C_8$ cycloalkoxy; or R is aryl, arylalkyl, heteroaryl, and heteroarylalkyl, the ring portion of each is unsubstituted or substituted with one, two, three, four, or five groups independently selected from the group consisting of lower alkyl, lower alkoxy, halogen, aryl, arylalkyl, trifluoromethyl, trifluoromethoxy, $C_3$–$C_8$ cycloalkyl, and $C_3$–$C_8$ cycloalkoxy;

R' is lower alkyl, alkoxyalkyl, cycloalkylalkyl, or arylalkyl wherein the aryl group is unsubstituted or substituted with one, two, three, four or five groups independently selected from the group consisting of lower alkyl, lower alkoxy, halogen, aryl, arylalkyl, trifluoromethyl, and trifluoromethoxy.

In another more preferred embodiment, R is selected from the group consisting of $C_1$–$C_6$ alkyl, $C_3$–$C_6$ cycloalkyl, aryl, and arylalkyl, each of which is unsubstituted or substituted with one, two, or three, groups independently selected from the group consisting of alkyl, alkoxy, halogen, trifluoromethyl, and trifluoromethoxy.

In another more preferred embodiment, R' is selected from the group consisting of $C_1$–$C_6$ alkyl, and arylalkyl wherein the aryl group is unsubstituted or substituted with one, two, three, four or five groups independently selected from the group consisting of alkyl, alkoxy, halogen, trifluoromethyl, trifluoromethoxy, and haloalkyl.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms can be obtained by asymmetric synthesis, using enantiomerically enriched starting materials or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

By "lower alkoxy" or "alkoxy" in the present invention is meant straight or branched chain alkoxy groups having 1–6 carbon atoms, such as, for example methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. These groups may be substituted with up to four groups mentioned below for aryl.

The term "alkoxyalkyl," refers to an alkoxy group, as defined above, attached to the parent molecular moiety through an alkyl group, which is defined below.

By "lower alkyl" or "alkyl" in the present invention is meant straight or branched chain alkyl groups having 1–6 carbon atoms, such as, for example, methyl, ethyl, propyl, isopropyl, n-butyl, sec-butyl, iso-butyl, tert-butyl, pentyl, 2-pentyl, isopentyl, neopentyl, hexyl, 2-hexyl, and 3-hexyl.

By "aryl" is meant an aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl), which is optionally mono-, di-, or trisubstituted with halogen, —OH, —SH, alkyl, alkoxy, alkylthio, trifluoromethyl, trifluoromethoxy, acyloxy, aryl, heteroaryl, amino, mono- or dialkylamino, and nitro. A preferred aryl group is phenyl.

The term "arylalkyl" refers to an aryl group, as described above, attached to the parent molecular moiety through an alkyl group, as defined above.

A "cycloalkyl" group is a nonaromatic cyclic ring or fused rings having from 3 to 7 members. Examples include cycloproply, cyclobutyl, and cycloheptyl. These rings may be substituted with one or more of the substituent groups mentioned below for aryl, for example, alkyl, halo, amino, hydroxy, and alkoxy. Typical substituted carbocyclic groups include 2-chlorocyclopropyl; 2,3-diethoxycyclopentyl; and 2,2,4,4-tetrafluorocyclohexyl. The carbocyclic group may contain one or two heteroatoms selected from oxygen, sulfur and nitrogen, and such ring systems may be referred to as "heterocylyl," or "heterocyclic." Examples include pyranyl, tetrahydrofuranyl, and dioxanyl. These heterocyclic groups may be substituted with up to four of the substituent groups mentioned for aryl to gives groups such as 3-chloro-2-dioxanyl, and 3,5-dihydroxymorpholino. In addition, the carbocyclic or heterocyclic group may also contain one or more internal double bonds, as long as having such double bonds does not make the carbocycle or heterocycle aromatic.

The term "cycloalkylalkyl" refers to a cycloalkyl group attached to the parent molecular moiety through an alkyl group, which is defined above.

By the terms "halogen" or "halo" in the present invention are meant fluorine, chlorine, bromine, and iodine.

In another more preferred embodiment, the method of the present invention is carried out at temperatures of from between −20° C. and 15° C. Most preferably, the reaction temperature is about 0° C.

In still another more preferred embodiment, the hydrogen chloride in dissolved in anhydrous 1,4 dioxane or anhydrous ethyl ether. Most preferably, the hydrogen chloride in dissolved in anhydrous 1,4 dioxane.

In yet another more preferred embodiment, the alcohol is selected from the group consisting of methanol, ethanol, propanol, isopropanol, butanol, sec-butanol, isobutanol, pentanol, sec-pentanol, benzyl alcohol and furfuryl alcohol. Most preferably, the alcohol is methanol or ethanol.

In another more preferred embodiment, the nitrile is treated with the anhydrous hydrogen chloride solution and the anhydrous alcohol in the presence of at least one suitable solvent. More preferably, the solvent is anhydrous ethyl ether.

In another more preferred embodiment, the product is isolated by trituration. The solvent used for the trituration is an ether. Most preferably, the solvent used for the trituration is ethyl ether or methyl t-butyl ether.

In still yet another more preferred embodiment, the slight excess of hydrogen chloride is removed by bubbling an inert gas into the reaction mixture.

In another more preferred embodiment, 2 to 8 equivalents of hydrogen chloride solution are used. More preferably, 4 equivalents of hydrogen chloride solution are used.

The disclosures in this application of all articles and references, including patents, are incorporated herein by reference.

The invention is illustrated further by the following examples, which are not to be construed as limiting the invention in scope or spirit to the specific procedures described in them.

The starting materials and various intermediates may be obtained from commercial sources, prepared from commercially available organic compounds, or prepared using well-known synthetic methods.

Representative examples of methods for preparing intermediates of the invention are set forth below.

EXAMPLES

Example 1

Synthesis of 1-methoxy-2-(3-methylphenyl) ethanimine (Compound 1)

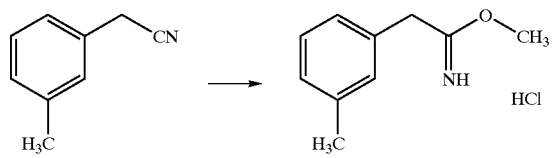

Cold 4 M hydrogen chloride in dioxane (184 ml, 0.763 mol) is added to a stirred and cooled (0° C.) mixture of 3-methylbenzyl cyanide (25 g, 0.19 mol) in anhydrous methanol (23 ml, 0.57 mol) and anhydrous ether (100 ml). The resulting reaction mixture is stirred at 0° C. for an additional hour and then it is placed in a refrigerator (0–5° C.) for 48 hours (during this time a small amount of white crystalline material precipitated). The reaction mixture is removed from the refrigerator and warmed to approximately 40° C. using a warm water bath. Nitrogen gas is then bubbled through the warm reaction mixture to remove excess hydrogen chloride. The volume of the solvent is reduced in vacuo, and anhydrous ether is added to effect precipitation. The precipitate is collected by filtration, washed with ether and dried under vacuum to afford 31 g (82%) of the crystalline imidate hydrochloride salt (1) as a white solid.

$^1$H NMR (CDCl$_3$): δ 12.82 (br s, 1H), 11.85(br s, 1H), 7.0–7.25(m, 5H), 4.25 (s, 3H), 4.0(s, 2H), 2.31 (s, 3H). $^{13}$C NMR (CDCl$_3$): δ 178.7, 139.3, 131.2, 130.5, 129.5, 129.3, 126.9, 61.3, 39.3, 21.6.

Example 2

Synthesis of 1,3-dimethoxypropanimine
(Compound 2)

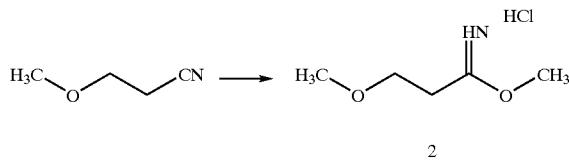

Cold 4M hydrogen chloride in dioxane (294 ml, 1.176 mol) is added to a stirred and cooled (0° C.) solution of 3-methoxypropionitrile (25 g, 0.294 mol) in anhydrous methanol (36.4 ml, 0.9 mol) and anhydrous ether (100 ml.) The resulting reaction mixture is stirred at 0° C. for an additional hour and then it is placed in a refrigerator (0–5° C.) for 48 hours (during this time a small amount of white crystalline material precipitated). The reaction mixture is removed from the refrigerator and warmed to approximately 40° C. using a warm water bath. Nitrogen gas is then bubbled through the warm reaction mixture to remove excess hydrogen chloride. The volume of the solvent is reduced in vacuo, and anhydrous ether is added to effect precipitation. The precipitate is collected by filtration, washed with ether and dried under vacuum to afford 38.7 g (86%) of the crystalline imidate hydrochloride salt (2) as a white solid.

$^1$H NMR (CDCl$_3$): δ 12.72(br s, 1H), 11.80(br s, 1H), 4.30(s, 3H), 3.80(t, J=5.65 Hz, 2H), 3.25(s, 3H), 2.95 (t, J=5.54 Hz, 2H). $^{13}$C NMR (CDCl$_3$): δ 178.9, 67.7, 61.3, 59.2, 34.0.

Example 3

The following compounds are prepared essentially according to the procedure of Examples 1 and 2 as described above. All compounds are isolated as white solids.

TABLE 1

| Structure | Amount prepared in grams (Yield %) | Name | Physical Data |
|---|---|---|---|
| 1 | 31 (82) | 2-m-Tolyl-acetimidic acid methyl ester hydrogen chloride salt | $^1$HNMR(CDCl$_3$): δ 12.82(br s, 1H), 11.85(br s, 1H), 7.0–7.25(m, 5H), 4.25(s, 3H), 4.0(s, 2H), 2.31(s, 3H). $^{13}$CNMR (CDCl$_3$): δ 178.7, 139.3, 131.2, 130.5, 129.5, 129.3, 126.9, 61.3, 39.3, 21.6. |
| 3 | 80 (82) | 2-(3-Fluoro-phenyl)-acetimidic acid methyl ester hydrogen chloride salt | $^1$HNMR(CDCl$_3$): 12.92(br s, 1H), 11.84(br s, 1H), 6.92–7.34(m, 4H), 4.25(s, 3H), 4.0(s, 2H). $^{13}$CNMR(CDCl$_3$): 178.0, 164.8, 161.5, 133.5, 133.4, 131.1, 131.0, 125.8, 125.7, 117.1, 116.9, 116.0, 115.7, 61.5, 38.9. |
| 4 | 33 (85) | 2-(4-Fluoro-phenyl)-acetimidic acid methyl ester hydrogen chloride salt | $^1$HNMR(CDCl$_3$): 12.72(br s, 1H), 11.78(br s, 1H), 7.52(m, 2H), 7.0(m, 2H), 4.30(s, 3H), 4.0(s, 2H). $^{13}$CNMR(CDCl$_3$): 178.4, 164.6, 161.4, 131.8, 131.7, 127.1, 116.5, 116.3, 61.4, 38.5. |
| 5 | 93 (76) | 2-(2-Fluoro-phenyl)-acetimidic acid methyl ester hydrogen chloride salt | $^1$HNMR(CDCl$_3$): 12.82(br s, 1H), 11.92(br s, 1H), 7.45(m, 2H), 7.25(m, 2H), 7.0(m, 2H), 4.25(s, 3H), 4.05(s, 2H). $^{13}$CNMR(CDCl$_3$): 177.9, 162.9, 159.6, 132.2, 132.1, 130.9, 130.8, 125.2, 125.1, 118.7, 118.5, 116.2, 116.0, 61.5, 33.0 |
| 6 | 56 (84) | 2-(2-Methoxy-phenyl)-acetimidic acid methyl ester hydrogen chloride salt | $^1$HNMR(CDCl$_3$): 12.42(br s, 1H), 11.95(br s, 1H), 7.25(br s, 1H), 6.95(br s, 1H), 4.20(s, 3H), 4.0(s, 2H), 3.84(s, 3H). $^{13}$CNMR(CDCl$_3$): 179.0, 157.6, 131.5, 130.0, 121.1, 120.0, 110.9, 61.1, 55.8, 34.7. |

TABLE 1-continued

| Structure | Amount prepared in grams (Yield %) | Name | Physical Data |
|---|---|---|---|
| 7 | 69 (86) | 2-(3-Methoxy-phenyl)-acetimidic acid methyl ester hydrogen chloride salt | $^1$HNMR(CDCl$_3$): 12.92(br s, 1H), 11.82(br s, 1H), 7.34(m, 1H), 7.12(m, 2H), 6.85(m, 1H), 4.25(s, 3H), 4.02(s, 2H), 3.85(s, 3H). $^{13}$CNMR(CDCl$_3$): 178.5, 160.3, 132.7, 130.4, 122.0, 115.5, 114.3, 61.4, 55.7, 39.3. |
| 8 | 112 (77) | 3-Methyl-butyrimidic acid methyl ester | $^1$HNMR(CDCl$_3$): 12.5(br s, 1H), 11.6(br s, 1H), 4.3(s, 3H), 2.6(d, J=7.2Hz, 2H), 2.2(m, 1H), 1.0(d, J=6.6Hz, 6H). $^{13}$CNMR(CDCl$_3$): 180.0, 60.8, 41.4, 27.0, 22.2. |
| 9 | 58 (91) | Cyclopentanecar-boximidic acid methyl ester hydrogen chloride salt | $^1$HNMR(CDCl$_3$): 12.3(br s, 1H), 11.4(br s, 1H), 4.2(s, 3H), 3.3(m, 1H), 2.0(m, 2H), 1.6(m, 6H),. $^{13}$CNMR(CDCl$_3$): 183.4, 60.9, 42.6, 31.0, 26.3. |
| 10 | 65 (91) | 4-Phenyl-butyrimidic acid methyl ester hydrogen chloride salt | $^1$HNMR(CDCl$_3$): 12.7(br s, 1H), 11.7(br s, 1H), 7.4(m, 5H), 4.4(s, 3H), 2.9(m, 4H), 2.2(m, 2H). $^{13}$CNMR(CDCl$_3$): 180.5, 140.4, 129.0, 128.9, 126.8, 61.1, 35.2, 32.9, 27.5. |
| 11 | 117 (79) | 2-Phenyl-acetimidic acid ethyl ester hydrogen chloride salt | $^1$HNMR(CDCl$_3$): 12.82(br s, 1H), 11.85(br s, 1H), 7.32(m, 5H), 4.25(s, 3H), 4.0(s, 2H). $^{13}$CNMR(CDCl$_3$): 178.6, 131.5, 129.7, 129.3, 128.5, 61.2, 39.2. |
| 12 | 56 (78) | 3-Methoxy-benzimidic acid methyl ester hydrogen chloride salt | $^1$HNMR(CDCl$_3$): 12.62(br s, 1H), 11.92(br s, 1H), 8.0(s, 1H), 7.85(m, 1H), 7.34(m, 1H), 7.23(m, 1H), 4.52(s, 3H), 3.95(s, 3H). $^{13}$CNMR(CDCl$_3$): 172.2, 3.95(s, 3H). $^{13}$CNMR(CDCl$_3$): 172.2, 160.3, 130.5, 126.3, 123.4, 122.2, 113.6, 61.7, 56.5. |
| 2 | 132 (76) | 3-Methoxy-propionimidic acid methyl ester hydrogen chloride salt | $^1$HNMR(CDCl$_3$): δ 12.4(br s, 1H), 11.6(br s, 1H), 4.30(s, 3H), 3.80(m 2H), 3.3(s, 3H), 2.97(m, 2H). $^{13}$CNMR (CDCl$_3$): δ 178.9, 67.5, 61.1, 59.0, 33.9. |
| 13 | 62 (93) | 2,2-Dimethyl-propionimidic acid methyl ester hydrogen chloride salt | $^1$HNMR(CDCl$_3$): 11.9(br s, 1H), 11.7(br s, 1H), 4.2(s, 3H), 1.3(s, 9H), (s, H). $^{13}$CNMR(CDCl$_3$): 185.8, 61.6, 39.0, 27.5. |

TABLE 1-continued

| Structure | Amount prepared in grams (Yield %) | Name | Physical Data |
|---|---|---|---|
| 14 | 61 (93) | 3-Phenyl-propionimidic acid methyl ester hydrogen chloride salt | $^1$HNMR(CDCl$_3$): 12.6(br s, 1H), 11.6(br s, 1H), 7.2(m, 5H), 4.2(s, 3H), 3.0(s, 4H). $^{13}$CNMR(CDCl$_3$): 179.7, 138.3, 129.0, 128.6, 127.2, 61.0, 34.8, 31.8. |
| 15 | 47 (67) | 4-Fluoro-benzimidic acid methyl ester hydrogen chloride salt | $^1$HNMR(CDCl$_3$): 12.7(br s, 1H), 12.0(br s, 1H), 8.5(m, 2H), 7.2(m, 2H), 4.5(s, 3H). $^{13}$CNMR(CDCl$_3$): 171.2, 169.4, 166.0, 133.3, 133.1, 121.5, 117.3, 117.0, 61.9. |
| 16 | 56 (78) | 4-Methoxy-benzimidic acid methyl ester hydrogen chloride salt | $^1$HNMR(DMSO-d$_6$): 11.82(br s, 2H), 8.25(d, J=6.5Hz, 2H), 7.15(d, J=6.4Hz, 2H), 4.45(m, 2H), 3.85(s, 3H), 1.34(t, J=7.2Hz, 3H). $^{13}$CNMR(DMSO-d$_6$): 170.4, 165.6, 132.4, 118.2, 115.3, 70.3, 56.8, 14.3. |
| 17 | 60 (92) | Cyclohexanecarboximidic acid methyl ester hydrogen chloride salt | $^1$HNMR(DMSO-d$_6$): 11.84(br s, 2H), 4.12(s, 3H), 2.72(m, 1H), 1.95(m, 5H), 1.32(m, 5H). $^{13}$CNMR(DMSO-d$_6$): 183.1, 61.0, 42.5, 29.2, 25.3, 25.2. |
| 18 | 59 (49) | 3-Fluoro-benzimidic acid methyl ester hydrogen chloride salt | $^1$HNMR(CDCl$_3$): 12.9(br s, 1H), 12.2(br s, 1H), 8.3(m, 1H), 8.0(m, 1H), 7.5(m, 1H), 7.4(m, 1H), 4.5(s, 3H). $^{13}$CNMR(CDCl$_3$): 171.2, 164.5, 161.2, 131.7, 131.6, 127.3, 127.2, 123.5, 123.2, 117.1, 116.8, 62.1. |
| 19 | 82 (92) | 2-p-Tolyl-acetimidic acid methyl ester hydrogen chloride salt | $^1$HNMR(CDCl$_3$): 12.6(br s, 1H), 11.5(br s, 1H), 7.2(m, 2H), 7.0(m, 2H), 4.1(s, 3H), 3.9(s, 2H), 2.2(s, 3H). $^{13}$CNMR(CDCl$_3$): 178.8, 138.4, 130.1, 129.8, 128.4, 61.3, 39.0, 21.4. |

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method for preparing imidoesters wherein the imidoester has the formula

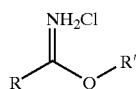

wherein

R is $C_1$–$C_{10}$ alkyl or $C_3$–$C_8$ cycloalkyl, each of which is unsubstituted or substituted with one, two, three, four, or five groups independently selected from the group consisting of lower alkyl, lower alkoxy, aryl, arylalkyl, trifluoromethyl, trifluoromethoxy, $C_3$–$C_8$ cycloalkyl, and $C_3$–$C_8$ cycloalkoxy; or R is aryl, arylalkyl, heteroaryl, and heteroarylalkyl, the ring portion of each is unsubstituted or substituted with one, two, three, four, or five groups independently selected from the group consisting of lower alkyl, lower alkoxy, halogen, aryl, arylalkyl, trifluoromethyl, trifluoromethoxy, $C_3$–$C_8$ cycloalkyl, and $C_3$–$C_8$ cycloalkoxy; and R' is alkyl, alkoxyalkyl, cycloalkylalkyl, or
   arylalkyl wherein the aryl group is unsubstituted or substituted with one, two, three, four or five groups independently selected from the group consisting of lower alkyl, lower alkoxy, halogen, aryl, arylalkyl, trifluoromethyl, and trifluoromethoxy, comprising:

A) treating a nitrile with an anhydrous hydrogen chloride solution and an anhydrous alcohol, and B) isolating the imidoester salt.

2. The method of claim 1 wherein the nitrile is treated with the anhydrous hydrogen chloride solution and the anhydrous alcohol at a temperature of from between –20° C. and 15° C.

3. The method of claim 2 wherein the temperature is about 0° C.

4. The method of claim 1 wherein the hydrogen chloride is in anhydrous 1,4 dioxane or anhydrous ethyl ether.

5. The method of claim 4 wherein the hydrogen chloride is in anhydrous 1,4 dioxane.

6. The method of claim 1 wherein the alcohol is selected from the group consisting of methanol, ethanol, propanol, isopropanol, butanol, sec-butanol, isobutanol, pentanol, sec-pentanol, benzyl alcohol and furfuryl alcohol.

7. The method of claim 6 wherein the alcohol is methanol or ethanol.

8. The method of claim 1 wherein the nitrile is treated with the anhydrous hydrogen chloride solution and the anhydrous alcohol in the presence of anhydrous ethyl ether.

9. The method of claim 1 wherein the product is isolated by trituration.

10. The method of claim 9 wherein the solvent used for the trituration is an ether.

11. The method of claim 9 wherein the solvent used for the trituration is ethyl ether or methyl t-butyl ether.

12. The method of claim 1 wherein any excess hydrogen chloride is removed by bubbling an inert gas into the reaction mixture.

13. The method of claim 1 wherein 2 to 8 equivalents of hydrogen chloride solution are used.

14. The method of claim 13, wherein 4 equivalents of hydrogen chloride solution are used.

15. A method of preparing a compound of the formula:

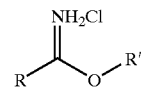

wherein
R is $C_1$–$C_{10}$ alkyl or $C_3$–$C_8$ cycloalkyl, each of which is unsubstituted or substituted with one, two, three, four, or five groups independently selected from the group consisting of lower alkyl, lower alkoxy, aryl, arylalkyl, trifluoromethyl, trifluoromethoxy, $C_3$–$C_8$ cycloalkyl, and $C_3$–$C_5$ cycloalkoxy; or R is aryl, arylalkyl, heteroaryl, and heteroarylalkyl, the ring portion of each is unsubstituted or substituted with one, two, three, four, or five groups independently selected from the group consisting of lower alkyl, lower alkoxy, halogen, aryl, arylalkyl, trifluoromethyl, trifluoromethoxy, $C_3$–$C_8$ cycloalkyl, and $C_3$–$C_8$ cycloalkoxy; and R' is alkyl, alkoxyalkyl, cycloalkylalkyl, or
   arylalkyl wherein the aryl group is unsubstituted or substituted with one, two, three, four or five groups independently selected from the group consisting of lower alkyl, lower alkoxy, halogen, aryl, arylalkyl, trifluoromethyl, and trifluoromethoxy;

the method comprising:

A) reacting a nitrile of the formula

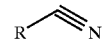

with an anhydrous hydrogen chloride solution in the presence of at least one solvent; and B) isolating the imidoester salt.

16. The method of claim 15 wherein
R is selected from the group consisting of $C_1$–$C_6$ alkyl, $C_3$–$C_6$ cycloalkyl, aryl, and arylalkyl, each of which is unsubstituted or substituted with one, two, or three, groups independently selected from the group consisting of alkyl, alkoxy, halogen, trifluoromethyl, and trifluoromethoxy.

17. The method of claim 15 wherein
R' is selected from the group consisting of $C_1$–$C_6$ alkyl, and arylalkyl wherein the aryl group is unsubstituted or substituted with one, two, three, four or five groups independently selected from the group consisting of alkyl, alkoxy, trifluoromethyl, and trifluoromethoxy.

* * * * *